(12) United States Patent
Robinson et al.

(10) Patent No.: US 12,402,862 B2
(45) Date of Patent: Sep. 2, 2025

(54) ULTRASOUND PROBE CONNECTED VIA A CABLE

(71) Applicant: KONINKLIJKE PHILIPS N.V., Eindhoven (NL)

(72) Inventors: Andrew Lee Robinson, Kenmore, WA (US); Antonia Cornelia Van Rens, Nuenen (NL); Alexander Ulrich Douglas, Goirle (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 82 days.

(21) Appl. No.: 18/024,123

(22) PCT Filed: Sep. 1, 2021

(86) PCT No.: PCT/EP2021/074082
§ 371 (c)(1),
(2) Date: Mar. 1, 2023

(87) PCT Pub. No.: WO2022/053362
PCT Pub. Date: Mar. 17, 2022

(65) Prior Publication Data
US 2023/0263506 A1      Aug. 24, 2023

Related U.S. Application Data

(60) Provisional application No. 63/075,756, filed on Sep. 8, 2020.

(51) Int. Cl.
*A61B 8/00* (2006.01)
*A61B 8/08* (2006.01)
(Continued)

(52) U.S. Cl.
CPC .............. *A61B 8/54* (2013.01); *A61B 8/4488* (2013.01); *G01S 7/5205* (2013.01);
(Continued)

(58) Field of Classification Search
CPC ... A61B 8/4444; A61B 8/4488; A61B 8/5269; A61B 8/54; A61B 8/56; A61B 8/58; G01S 15/8915; G01S 7/5205; G01S 7/5208

See application file for complete search history.

(56) References Cited

U.S. PATENT DOCUMENTS

| 4,306,313 A | 12/1981 | Baldwin |
| 5,517,994 A | 5/1996 | Burke et al. |

(Continued)

FOREIGN PATENT DOCUMENTS

| EP | 3839559 A1 | 6/2021 |
| JP | 2003210458 A | 7/2003 |
| JP | 2005253627 A | 9/2005 |

OTHER PUBLICATIONS

International Search Report and Written Opinion for PCT/EP2021/074082, Mailing date: Dec. 9, 2021, 9 pages.

*Primary Examiner* — Michael T Rozanski

(57) ABSTRACT

The invention is directed to an ultrasound probe (1) configured to be operatively coupled to a cable (10), the cable (10) comprising a plurality of lanes adapted to carry signals between the ultrasound probe (1) and a data processing unit, which is adapted to process the signals, in particular to beamform the signals and to reconstruct ultrasound images of an imaging region. The ultrasonic probe (1) comprises a transducer head comprising a plurality of transducer elements, which are adapted to insonify the imaging region according to an insonification scheme and to receive ultrasound signals, and a controller adapted to, responsive to the information of a faulty lane from a fault detection module adapted to detect integrity of each of the plurality of lanes, redistribute and/or reconfigure the signals carried by the faulty lane onto one or more of the non-faulty lanes.

20 Claims, 4 Drawing Sheets

(51) Int. Cl.
*G01S 7/52* (2006.01)
*G01S 15/89* (2006.01)

(52) U.S. Cl.
CPC ........ *G01S 7/5208* (2013.01); *G01S 15/8915* (2013.01); *A61B 8/5269* (2013.01)

(56) References Cited

U.S. PATENT DOCUMENTS

| | | |
|---|---|---|
| 5,709,209 A | 1/1998 | Friemel et al. |
| 2015/0050015 A1 | 2/2015 | Levy et al. |
| 2017/0219704 A1 | 8/2017 | Call et al. |
| 2020/0088862 A1 | 3/2020 | Lundberg et al. |

ULTRASOUND PROBE CONNECTED VIA A CABLE

CROSS-REFERENCE TO PRIOR APPLICATIONS

This application is the U.S. National Phase application under 35 U.S.C. § 371 of International Application No. PCT/EP2021/074082, filed on Sep. 1, 2021, which claims the benefit of U.S. Provisional Patent Application No. 63/075,756, filed on Sep. 8, 2020. These applications are hereby incorporated by reference herein.

FIELD OF THE INVENTION

The invention relates to an ultrasound probe configured to be connected to a data processing unit via a cable, a corresponding ultrasound system and a method for operating an ultrasound probe.

BACKGROUND OF THE INVENTION

Ultrasound (US) probes typically comprise an array of transducer elements that transmit and receive ultrasonic waves. Beamformers are used to appropriately delay and sum the echo signals that are received by the elements of the transducer array. The delays are usually chosen in consideration of the direction and focus depth of the beams to be formed by the beamformer. The delayed signals are combined to form a beam of properly steered and focused coherent echo signals.

In a traditional ultrasound system, the array transducer is located in the US probe which is placed against the body of the patient during imaging, and which may contain some electronic components such as switches and amplification devices. The delaying and signal combining is usually performed by the beamformer which is contained in the ultrasound system console, to which the probe is connected by a cable. Accordingly, a large amount of raw echo signals is usually transferred from the probe to the US system console through the cable. Therefore, the cable needs a sufficiently high capacity to transfer the required data rates as well as several data paths (in the following denoted as lanes), e.g. formed by wires, to transfer the numerous signals from the numerous transducer elements.

For some US probes, cable reliability is a major driver of overall reliability. Although the reliability of current transducer cables is generally high, some cables may still experience broken wires. Some wire breaks are relatively benign. For example, if the signal from each of 128 transducer elements is transferred on one of 128 cables, the loss of one cable is relatively unlikely to be clinically detectable. On the other hand, when a conductor performs a unique function, such as a power line or programming line, a single break may cause the entire transducer to fail. Digital US probes may be more susceptible to wire breaks than analogue US probes, because each conductor will generally carry signals from more than one transducer element. Improved reliability can generally be addressed by making wires larger, but that has a negative impact on ergonomics and may increase cable costs.

In some cases, fault tolerance for unique functions can be provided with redundant wires. For example, U.S. Pat. No. 4,306,313 A, which relates to an optical transmission system, proposes two or more optical fibers for a signal to be transmitted and the possibility to switch between these redundant fibers. This may be appropriate when the number of redundant fibers required is relatively small. However, a US probe typically requires cables with a larger number of wires in order transmit the large amount of data produced by the various elements of its transducer array and it is thus generally not practical to duplicate all of the wires in the cable.

OBJECT OF THE INVENTION

It is, therefore, an object of the invention to provide an ultrasound probe, an ultrasound system and a method that provide a solution wherein the cable connection between a probe and a processing unit of the US system is fault-tolerant, in particular fault tolerant for breaks of signal paths, while maintaining favorable ergonomics.

SUMMARY OF THE INVENTION

This object is met or exceeded by an ultrasound (US) probe according to claim 1, an ultrasound system according to claim 8 and a method for operating an ultrasound probe according to claim 15. Any features, advantages or alternative embodiments described herein in relation to the claimed ultrasound probe are also applicable to the ultrasound system and the method and vice versa.

According to the invention, an ultrasound probe is provided that is configured to be operatively coupled to a cable, the cable comprising a plurality of lanes adapted to carry signals between the ultrasound probe and a data processing unit, which is adapted to process the signals, in particular to beamform the signals and to reconstruct ultrasound images of an imaging region. The ultrasonic probe comprises
- a transducer head comprising a plurality of transducer elements, which are adapted to insonify the imaging region according to an insonification scheme and to receive ultrasound signals; and
- a controller adapted to receive information on the integrity of each of the plurality of lanes from a fault detection module, which is adapted to detect integrity or faultiness of each of the plurality of lanes, and wherein the controller is adapted to, responsive to the information of a faulty lane from the fault detection module, redistribute and/or reconfigure the signals carried by the faulty lane onto one or more of the non-faulty lanes.

The invention provides fault tolerance for the break/faultiness of at least a single lane, and in some embodiments even provide immunity to more than one broken conductor or faulty lanes. Some embodiments have no performance impact, other embodiments require performance compromises.

The US probe of the invention comprises a transducer head and generally a transducer handle and/or housing with some electronics (e.g. including the controller), but not a cable. The US probe is also referred to as transducer sensor assembly. In a preferred embodiment, the ultrasound probe is a digital US probe, also referred to as digital transducer. Digital US probes generally tend to be more susceptible to wire breaks than analogue US probes because more of the conductor lanes perform a unique function, in particular the signals from several transducer elements are often transferred via one lane. Furthermore, digital signals are easier to reconfigure than analogue signals. The digital US probe preferably comprises an in-probe analogue-to-digital converter (ADC), to convert the analogue echo signals received by the probe into digital signals. Preferably, in the digital US probe some electronics are available at both ends of the cable, wherein the transducer end preferably has sufficient electronics to support the signal redistribution and/or reconfiguration described herein upon detection of a faulty lane. However, the US probe of the invention may also be an analogue US probe. The US probe is preferably adapted for medical US imaging. However, the concept of the invention is mainly concerned with cable faults and can thus be applied to any kind of US probe that is connected via a cable. For example, US probes concerning the examination of technical structures or underwater US probes are also within the scope of the invention. The US probe is configured to be connected to a cable, in particular via connectors, preferably electric connectors, that are part of the US probe. In this sense, the cable may be detachably connected to the probe. However, it is also conceivable that the cable is permanently connected to the probe.

Preferably, the lanes are to be understood as signal paths of the cable, in particular digital or analogue signal paths. The lanes carry the echo signals (also referred to as ultrasound signals) received by the transducer elements to the data processing unit, and will in most embodiments also carry control signals such as configuration information, e.g. information on the transmit scheme, from the console (e.g. the data processing unit) back to the US probe, in particular to the electronics in the transducer handle. A lane may carry control signals, ultrasound signals, or both. The lanes are preferably implemented as conductors, but may also be optical signal lanes, e.g. optical fibres. Where the lanes are electrical signal paths, they may be implemented e.g. as coaxes or twisted pairs. The invention is generally applicable to both single-ended signal paths, i.e. having one ground potential or reference wire and one signal wire, and differential signal paths, i.e. having two complementary signals and which depend on the signals' electrical difference. In the case of an electric cable, the lanes may be formed by an assembly of wires and/or conductors that are, for example, arranged side by side or bundled. In one example, the cable may comprise of a number of thin coaxes, e.g. 128 thin coaxes, in particular analogue coaxes. However, it may be beneficial to have digital signal paths, e.g. each lane being formed by a twisted pair, which may provide a high-speed data connection. Transfer rates (streams) of about 5 Gb or more per second are commonly required for each lane. If implemented electrically, the data rate in a single lane may be in the range of 4 to 8 Gb per second.

Preferably, a lane is used to carry (only) digital signals/data. However, the invention is also applicable to transducer/cable configurations in which a given set of conductors is used to carry multiple types of signals, such as power being carried on a twisted pair, which may also be a digital lane. Accordingly, the fault detection module may include a current sensor which monitors the current on each conductor carrying power; if the current is zero when it should not be, the power is switched to a spare conductor. In this embodiment, a "lane" may also be conductor carrying power. The current sensor may be implemented by a current sense resistor included in a voltage regulator.

In other embodiments, power is supplied to the US probe via a separate conductor (which is not a lane), or by a (rechargeable) battery, in particular a battery included within the US probe. The lanes may be made of wires consisting of a conductive material, such as Cu, Al or a metal alloy. Furthermore, the wires of the lanes may be plated with a thin layer of another metal, such as e.g. Zn, Au, Ag, to provide protection from oxidation. In order to provide protection from cross interference, the lanes may be shielded with respect to each other and/or with respect to the environment, for example they may be arranged in a coaxial and/or twisted-pair geometry. The lanes are not restricted to being made of electric wires. It is also conceivable that the lanes are adapted to carry signals in a different way, for example optical signals may be carried by optical fibres. In this case, the lanes might be optical pathways.

The term plurality of lanes refers to there being more than one lane. For example, there may be a total of 4-128, preferably 8-40 lanes, and more preferably 16-32 lanes, comprised in the cable. The lanes are adapted to carry signals, which may e.g. be digital or analogue signals. The signals may be in the form of electric currents or of optical signals. The signals coming from the probe may be mostly created by the transducer elements from received echo signals, optionally converted by an ADC. Preferably, signals from a plurality of transducer elements are transmitted on each lane, e.g. echo signals from 4 to 60 transducer elements may be transmitted per lane.

The data processing unit is preferably part of an US system console. It may also be part of or may be a computer or a laptop, or a smaller device such as a tablet, a PDA or a smart phone, e.g. provided with the Philips Lumify©-App. Preferably the data processing unit is thus not part of the US probe itself, but is connected to the US probe via the cable. However in some cases, in particular if the system console has limited processing power, e.g. in case of the Lumify©-App on a tablet, it may be preferable to provide the data processing unit within the US probe. The data processing unit preferably comprises a system interface, in particular a digital system interface, with a data connection for one or several lanes. The data processing unit is adapted to receive and further process the signals transferred through the cable from the US probe, in particular to at least partially beamform the echo signals and/or to perform signal processing and image processing, and possibly to store the US images digitally. In some embodiments, the beamforming may be partially carried out within the US probe, and the partial beamsums are transmitted to the data processing unit to complete beamforming, signal processing and image processing. The data processing unit is preferably connected to a user interface, which is adapted to display US images to a user and which may allow the user to change or adjust image or measurement parameters and/or the insonification scheme and/or switch between different modes, such as B-mode or Doppler imaging. If the US probe is used for medical applications, the imaging region may for example be within an anatomical structure, such as an organ, the head or a limb or part thereof, of a human or animal body.

The transducer head preferably comprises an array of transducer elements (array transducer). It may for example be a 1D array with a fixed mechanical focus to electronically steer and focus in azimuth for two-dimensional imaging. In this case there are preferably at least 64 transducer elements, more preferably 128 or more, in particular 128 to 960. The transducer elements may also be arranged in a 2D array, wherein the transducer elements may electronically steer and focus beams in both azimuth and elevation over a volumetric region, thus enabling three-dimensional imaging. In this case the number of transducer elements is typically higher, preferably more than 2500 and up to 100.000, more preferably up to 60.000.

The transducer elements of the transducer head are adapted to insonify the imaging region and to receive ultrasound signals, in particular in the form of echo signals reflected from the imaging region. Insonifying the image region may be understood as emitting controlled US pulses by the plurality of transducer elements into the imaging region. In this context the insonification scheme may be a transmit and receive scheme of the transducer head comprising various parameters, e.g. temporal resolution (i.e. time intervals between transmit events, frame rate, sampling frequency), focusing scheme, depth range, penetration depth, spatial resolution, size of imaging region, contrast and/or field of view. Furthermore, different beam forming modes may be applied, such as multi-line acquisition (MLA), multi-line transmission (MLT), plane, wave, diverging wave, and/or synthetic aperture beam forming.

The fault detection module may be disposed at either end of the cable, i.e. it may be part of the US probe, or it may be part of an ultrasound console to which the probe is connected via the cable, e.g. it may be part of the data processing unit. The response to the detected faults may be coordinated between console and US probe (transducer) to maintain correct operation of the ultrasound system as a whole, but the detection and management of the fault response can be at either end (console or US probe). Since there is typically more space and power available in the console, the fault detection module is preferably part of the console, and the information on the integrity of the lanes is thus transferred through one or several of the lanes to the controller on the US probe. On the other hand, disposing the fault detection module in the US probe has the advantage that the information on lane integrity cannot be lost by the faultiness of the lane transmitting this very information. The fault detection module may be a separate part in the probe, or may be a part of the controller.

The fault detection module is adapted to detect information on the integrity or faultiness of each of the plurality of lanes. This may be achieved by a self-check of the ultrasound probe via the fault detection module, in particular when initiating operation of the ultrasound probe or after a connection to the data processing unit. Therewith, the correct functioning of a yet untested cable may be verified. Damages, such as wire breaks, that may have occurred during storage or transport of the cable may be discovered and a possible impact on the measurement may be analyzed within the scope of the self-check or by a user who may be notified of any cable faults. Checking the lanes may also be carried out repeatedly, e.g. by periodically sending a test signal on a lane, which may be detected at the distal end, and analyzing the result. For example, a fault detection module on the US probe may send test signals to the data processing unit and vice versa, i.e. as a "hand-shake". Information whether this signal has arrived may subsequently be sent back to the sender of the test signal. A continuous testing, e.g. at pre-determined intervals, allows for faulty lanes occurring during the operation to be detected more or less immediately, e.g. when the cable is bent unduly or pressure is exerted on the cable. In case of digital lanes, fault detection is also possible by detecting errors in the transferred digital signal, e.g. since the signal (i.e. the data to be transferred) is encoded in a pre-determined way. Encoded data (the transferred digital signal) has certain characteristics such as inclusion of comma codes and follows a certain protocol. Data on a faulty lane will not show these characteristics or will include relatively high number of abnormalities.

The fault detection module may detect irregularities in the connection via the cable or be notified about irregularities in the connection, i.e. receive information concerning a faulty lane, e.g. from the data processing unit. Irregularities may for example be missing or invalid signals. For example, test signals may be sent through the different lanes of a connected cable. In this case the data processing unit may answer to received test signals and any unanswered or invalid signal may be noted. The invention is generally applicable in this sense, if there are electronics at both ends of the cable. Alternatively, test signals may be reflected from a faulty location in the faulty lane. For example, the fault detection module might measure the travel time of a test signal in order to determine the fault and possibly its location. This allows for the fault detection module to determine faulty lanes without needing to communicate for this purpose with another device, such as the data processing unit. It is also conceivable that the testing of the cable is carried out by the data processing unit (which thus incorporates the fault detection module) and a notification is sent to the controller in case of a faulty lane. The data processing unit or fault detection module may detect errors with the help of check sums or specific encodings sent together with the signals that may reveal the absence of data or individual signals. A check sum may for example be sent on an additional lane, reserved for the transmission of the check sum. The data processing unit or fault detection module in the console may also be able to determine the existence of a faulty lane from a decreased performance, e.g. a decreased data rate or a decreased image quality. Another measure may be, to add redundancy to the data distributed over a number of lanes, i.e. an extra lane that comprises some information of all signals from all the other lanes. Hence, if some data are not reaching the data processing unit due to a faulty lane, it may be immediately noticed by comparison with the data from the extra lane. Therefore, this redundancy may simplify the detection of missing data. Detection of the faulty lane by the data processing unit (comprising the fault detection module) may have the advantage that the data processing unit does not have to be notified in order to adapt to the changed situation that accompanies a faulty lane. Power connections or analogue signals may be monitored by observing the current through these respective lanes, e.g. by a voltage regulator with a current sense resistor. In this case, if the current is zero when it should not be zero, the fault detection module will notice that the power lane is faulty.

The controller is preferably connected to the fault detection module. It may also be directly or indirectly connected to the transducer head. The controller is part of the electronics in the US probe and may in particular be part of an application-specific integrated circuit (ASIC) of the ultrasound probe. In an embodiment, both the controller and the fault detection module may be part of the ASIC. The controller may comprise a processor that may be adapted to process information received from the fault detection module and/or the data processing unit via the cable. Furthermore, the controller may comprise a data storage device, such as RAMs, ROMs, disk drives or flash memory. The controller may contain programmed rules and/or decisions and/or algorithms on how to operate the transducer head and/or how to distribute data from the transducer head onto the different lanes of the cable, in particular in the case of the detection of a faulty lane. This allows the controller to operate automatically and without any additional input from a user and/or the data processing unit. The controller is adapted to be responsive to information of a faulty lane and take action as a reaction to the detection of a faulty lane. E.g., the US probe may identify the number of available/operational lanes on power-up via the fault detection module and the controller may configure the communication via the cable accordingly. Preferably, the controller is configured to coordinate the redirection and/or reconfiguration of the signals with the console, in particular the data processing unit, e.g. by sending respective messages on the selected response to the fault detection to the data processing unit. It is conceivable that the controller is configured to receive commands from the data processing unit. For example, the controller may be adapted to be optionally and/or partially controlled by a user via a user interface that is connected to the data processing unit. The controller may be configured to send messages and/or information to the user via the cable and a user interface connected to the data processing unit. The controller may also be configured to send an alert to a user via a user interface or via notification means, e.g. an alert indicator or an alarm light, at the ultrasound probe. This allows the US probe to be independent of the US system console or the data processing unit in terms of notifying the user. Alternatively, the controller may also be configured to notify the user via the cable and a user interface connected to the data processing unit. Hence, the user may see the alert directly at the user interface he or she is operating and watching during the operation of the US probe and during the analysis of the US images. Preferably the controller may carry information about the cable and/or lane capacity, i.e. the data rate, and/or the actual current use of the capacity at the moment. I.e., the controller may carry information about how much data can be transferred through each lane of the cable, how many (operational) lanes the cable has, and what is the currently needed data rate for each signal transmitted via the cable.

In the event of a detected faulty lane and after being notified about such an event, the controller is adapted to redistribute and/or reconfigure the signals carried by the faulty lane onto one or more of the non-faulty lanes. The redistributed and/or reconfigured signals are the control signals and/or the echo signals, preferably both, wherein the echo signals transferred from the probe to the data processing system typically comprise more data and thus require more redistribution and/or reconfiguration. Preferably, this is done automatically, i.e. the user, at least initially, does not have to actively choose an appropriate reaction to the faulty lane. In particular, redistribution of a signal may be understood as redirecting and/or rerouting the signal to one or more other (non-faulty) lane(s). This may imply rerouting the signal from the faulty lane to another (e.g. redundant) lane. It may also mean that the controller is adapted to combine signals from several lanes to be transferred on one (or several) other lane(s). E.g., the controller may be adapted to add the signal from the faulty lane to another signal that is to be transferred by that other lane. This allows a flexible adaption to the current situation depending on the status of the cable and the requirements and specifics of the measurement. The controller may also be adapted to cause transferring the signal from the faulty lane to another lane during time intervals when the original signal of this other lane produces no data rate, e.g. periodically according to a measurement and/or insonification scheme. This option is described in more detail below, as it requires digitization of the signal and the use of memory to temporarily store the digital data. This allows for an optimum use of the available data rate capacity of the cable's lanes. In particular if the capacity of the non-faulty lanes is not sufficient to carry all the signals including the signal from the faulty lane, the controller may be adapted to reconfigure the signal from the faulty lane and/or one or several signals from one or several non-faulty lanes. Reconfiguration of signals may be understood to mean changing the signal in some way, including buffering signals. Hence, the controller may adapt to the situation of the available capacity of the lanes not being sufficient to transfer all the data due to a faulty lane. For example, the controller may be adapted to cause some data not to be transferred, if necessary. This data may be the data originally transferred on the faulty lane, but it also is possible to transmit the data of the faulty lane across a non-faulty lane and skip the original data of the non-faulty lane, if the data of the faulty lane is more relevant for the particular insonification event. Such an omission of data may possibly lead to a reduction in image quality, but may on the other hand be a valid option, if the omitted data is not essential for the measurement, e.g. if the signal from one or several transducer elements is not vital for the required beamforming process, or if a particular beam is directed to a peripheral region of the imaging region, while the important parts of the observed structure are placed more centrally in the imaging region. It may also be conceivable that the controller is adapted to distribute signals, in particular a signal from the faulty lane, from one lane to two or more different lanes, i.e. to split the signal. The controller may also be adapted to automatically reduce the sampling rate of a signal, e.g. the signal from the faulty lane. This may be an option if the sampling rate does not need to be as high as originally set for the particular insonification scheme chosen by the user. The controller may also be adapted to modify the time during which individual signals are transferred through the cable. For example, the controller may be adapted to initiate buffering of data, possibly buffering the data from the faulty lane and arranging it to be sent during dead time of a lane's original signal. The dead time may in particular refer to the time between the end of one receive event and the beginning of the next transmit event. The dead time in each transmit/receive cycle may be in the range of 1 μs to 50 μs, preferably 4 μs to 25 μs. Sending data during dead time serves as an effective measure to optimally use the available data rate, and possibly redistribute information from the faulty lane without any or with only little loss of image quality or frame rate. It also is possible to lower the pulse repetition rate of the insonification scheme (and thereby the framerate) in order to increase the available "dead time".

If the US probe includes an analogue-to-digital converter (ADC), the controller may also be adapted to lower the resolution of the ADC, if necessary. It is also possible to reduce the resolution of the ADC only during a particular section of an acquisition cycle, for example when looking into deep tissue, where the dynamic range of the data is reduced already. Preferably, the US probe is configured to send corresponding information to the data processing unit, when the data format is changed or the signals are reconfigured or redistributed. This ensures that the data processing unit may adapt to and be able to process the changed signals. It is also conceivable that the controller receives instructions from the data processing unit. In particular the controller may receive instructions concerning the redistribution and/or reconfiguration of the signals. Hence, algorithms and decision patterns in the case of a faulty lane may be stored on the data processing unit and transmitted to the controller when applicable. Alternatively or additionally, instructions may be input by a user at a user interface connected to the data processing unit. This allows the user to adapt the measurement according to his own requirements to best overcome the drawbacks that may come with a reduced data rate due to a faulty lane.

According to an embodiment, the controller is adapted to redistribute the signals by re-routing the signals carried by the faulty lane to a redundant lane of the plurality of lanes; or, if no redundant lane is available, to modify the signals carried by the one or more non-faulty lanes so as to include information related to the signal originally carried by the faulty lane. In this context a redundant lane may be understood as a lane that is functional and available, i.e. provides a connection between the US probe and the data-processing unit, but is originally not needed for the operation of the US probe and the transmission of signals. E.g., there may be extra/redundant coaxes or twisted pairs. This may for example be the case, when standardized cables are used that are compatible with different systems, but not all systems and/or US probes need all the available lanes for their standard operation. In other words, it may be beneficial to have a standard cable that may be used on several different US probes, and the capacity of this cable may need to be sufficient to meet the requirements of the most demanding US probe, i.e. the US probe that produces the highest data rate. Hence, the data rate of the lanes or the number of lanes may be greater than what is needed for many or even most US probes. E.g., among n US probes that use the standard cable, n-1 US probes or a number of US probes between n-1 and 1 will have some excess capacity when using the standard cable. On the other hand, it is also conceivable that, depending on the measurement mode and/or the insonification scheme that is used for a current measurement, the amount of data and thus the number of needed lanes may vary. Therefore, during a specific measurement, there may be redundant lanes that are not needed for this specific measurement. Re-routing to a redundant lane has the advantage of not having to make any compromise regarding image quality or frame rate because the redundant lane can just replace the faulty lane. In other words, if a redundant lane is available the controller may re-route the signals carried by the faulty lane to such a redundant lane without any significant impact on performance, in particular without any reduction in data rate and thus without a reduction in image quality and frame rate. It may even be beneficial to intentionally plan to have redundant lanes. While this may add costs and increase the size of the cable, it may still be preferable when compared to having an increased size of every lane in order to achieve a desired or necessary level of cable reliability. Even a single redundant lane, e.g. 25 lanes instead of 24 lanes, may greatly improve the reliability of the cable. However, a larger number of additional/redundant lanes may be more beneficial, in order to open new applicational uses of a thus modified cable with respect to the original cable, e.g. the cable with 24 lanes.

If, however, no redundant lane is available the information from the faulty lane may be partially or completely included in a signal carried by a non-faulty lane. This may in particular be an option, if the non-faulty lane still has enough capacity to increase the data rate. Hence, the data rate of one or several or all remaining lanes may be increased. The information from the faulty lane may also be split and added to signals from different non-faulty lanes, e.g. if the data rate of one lane is not sufficient to carry its original information and the complete information added from the faulty lane. If necessary, the information from the faulty lane may also be changed, in particular reduced, in order to decrease the data rate, prior to adding it to one or several other signals. Preferably such a reduction of data will lead to the omission of non-essential data. Preferably, such omission may lead to a non-noticeable or small decrease of the image quality of the US image. It may even be an option to completely omit the data from the faulty lane, depending on how important the information is for the measurement and its analysis. Such an omission may lead to a reduction in image quality or refresh rate. On the other hand, it may also be an option to redistribute the complete information from the faulty lane. In this case the image quality may be maintained, but a reduction of the refresh rate may occur, i.e. the rate in which the ultrasound signal data are processed and US images are reconstructed by the data processing system and displayed to the user is reduced. The refresh rate may relate to complete images (frames), or to individual lines therein, i.e. it may occur that some lines in an image are refreshed less often than the other lines. Such reduction in refresh rate may occur automatically if the signals are transferred through the cable at a slower data rate. A reduction in frame rate may also be achieved by changing the insonification scheme, which is typically initiated by the data processing unit. In some cases, a reduction in frame rate or refresh rate may partially or completely be counteracted by buffering at least some of the data and optimizing the timed schedule of when signals are sent through the lanes, e.g. minimizing dead time during which temporarily no data is sent. In the case of digital signals, it is also conceivable to reduce the resolution or sampling frequency of the ADC, e.g. to align the number of samples with the number of remaining lanes and desired frame rates. Any of these reconfiguration or modification methods as well as any variants described later may be applied individually or in any combination with one another. The exact nature of the combination may depend on the needs of the current measurement. It may also be applicable to combine the re-routing to the redundant lane and the redistribution/modification, for example if the data rate capacity of the redundant lane is lower than the data rate of the signal that was originally to be led through the faulty lane and/or if there are several faulty lanes and the number of faulty lanes is higher than the number of redundant lanes.

Preferably, the controller is adapted to do the reconfiguration and/or redistribution while maintaining the quality of the ultrasound images and/or the refresh rate of the ultrasound images above predefined thresholds. Hence, the controller may have stored these predefined thresholds in order to maintain a predetermined image quality and/or refresh rate (or frame rate). In this way it can be made sure, that a prioritization of different reconfiguration schemes, such as omission or reduction of the signal data, is done in a predetermined way that has the least impact on the diagnostic value of the US measurement, in particular US images. E.g., if a certain refresh rate (or frame rate) is essential for the measurement, for example because part of an observed organ moves with a certain velocity, it is made sure that the refresh rate remains high enough to still allow observation of this movement. In this case, if the threshold for the refresh rate is reached, the refresh rate would not be lowered any more, but other parameters related the image quality, might be lowered instead. At the same time, it may for example also be made sure that the resolution remains high enough to distinguish different essential features in the imaged region.

According to an embodiment, the US probe comprises an analogue-to-digital converter (ADC) configured to convert the signals received by the transducer elements into digital signals, wherein, responsive to the information of a faulty lane from the fault detection module, the analogue-to-digital converter is adapted to decrease its bit depth or sampling frequency, and the controller is configured to redistribute the signals carried by the faulty lane to at least some of the non-faulty lanes and to modify the signals carried by the non-faulty lanes so as to include digital signals originally carried by the faulty lane. Preferably, the ADC is arranged as an array of ADCs which may correspond to the array arrangement of the transducer elements. For example, if originally a 12-bit precision is used, the converter may be adapted to decrease its bit depth to an 8-bit precision. Advantageously, the rate at which the signal data is produced may thus be decreased due to the lower bit depth or sampling frequency, therefore compensating for the reduction of available lanes when one or more lanes are faulty. The lower data rate may then allow to combine signals from different lanes, e.g. from a faulty lane and a non-faulty lane, onto one single lane.

According to another embodiment, responsive to the information of a faulty lane from the fault detection module, the controller is configured to modify the signals carried by the non-faulty lanes so as to include digital signals originally carried by the faulty lane, wherein the modification includes the suppression of the least-significant bit or bits of each digitized signal sample. The least significant bits are the one for the smallest powers of two, i.e. $2^1$ or $2^0$. The least significant bit is usually the one that carries the least important information and the most random measurement noise. Hence its omission might allow for a reduction in data rate while at the same time having only little impact on the image quality and the accuracy of measurement.

According to an embodiment, the US probe comprises an analogue-to-digital converter configured to convert the signals received by the transducer elements into digital signals, and an in-probe memory configured to buffer digital signals, wherein, responsive to the information of a faulty lane from the fault detection module, the controller is configured to redistribute the signals carried by the faulty lane to at least some of the non-faulty lanes by modifying the signals carried by the non-faulty lanes so as to include digital signals originally carried by the faulty lane, and wherein the in-probe memory is adapted to buffer at least a part of the digital signals received from the analogue-to-digital converter during a receive event of the transducer elements, and wherein the controller is adapted to stream out the buffered digital signals also during dead time of the transducer elements, in particular in the dead time between the end of one receive event and the beginning of the following transmit event. Hence, part of the data may be streamed out through the lanes right after the corresponding echo signals have been received by the transducer elements and processed by the ADC, while another part of the data may be buffered and streamed out through the lanes during dead time. Using dead time allows for a more efficient use of the available data rate and minimizes the decrease in image quality and refresh rate.

According to one embodiment, the in-probe memory is adapted to buffer a part of the digital signals from some or all of the transducer elements, and to stream it out during dead time. Thus, all signals (or signal channels) may equally be buffered. According to another embodiment, the in-probe memory is adapted to buffer the digital signals originally carried by the faulty lane while the transducer elements are receiving ultrasound signals, and the controller is adapted to stream out the buffered digital signals originally carried by the faulty lane during dead time of the transducer elements. Hence, data from the faulty lane is buffered and sent out, when the most capacity in the lanes of the cable is available. Herewith, as much information as possible from the signal that originally was supposed to be transferred via the faulty lane may be transmitted.

According to another aspect of the invention, an ultrasound system is provided comprising an ultrasound probe according to any one of the preceding claims, a data processing unit, which is adapted to process signals received from the ultrasound probe, in particular to beamform the signals and to reconstruct ultrasound images of an imaging region; a fault detection module adapted to detect information on the integrity of each of the plurality of lanes; and a cable operatively coupled to the ultrasound probe, the cable comprising a plurality of lanes adapted to carry signals between the ultrasound probe and the data processing unit. The US system also comprises a fault detection module as described herein, which may be disposed in the US probe or in a console of the US system. All the advantages and features described for the US probe are also applicable to the US system and vice versa. The US system is preferably a medical imaging system, and may further include a user interface including a display and a user input device such as a touchpad, keyboard, mouse and/or trackball etc.

According to an embodiment, the response of the controller to the detection of a faulty lane may also be to increase the data rate on the non-faulty (functional) lanes in order to include the data of the faulty lane. This is applicable in particular if the signals are transferred as digital data through a high-speed link.

According to an embodiment, if the quality of the ultrasound images and/or the refresh rate cannot be maintained above predefined thresholds by reconfiguration and/or redistribution of the signals after detection of a faulty lane, the system is adapted to change the insonification scheme so that the predefined thresholds are met. Hence some parameters may be lowered in order to enable important parameter to remain above essential thresholds. The change of the insonification scheme may be initiated by the controller, i.e. in the US probe, or by the console, e.g. the data processing unit.

The system may be adapted to change the insonification scheme by one or more of reducing the frame rate, reducing the sampling frequency, decreasing the spatial resolution or reducing the size of the imaging region. In this context, the system may be adapted to change the insonification scheme while taking account of predefined thresholds, or alternatively independent of predefined thresholds. In particular, the system may be adapted to take any of these measures, if, after the occurrence of a faulty lane, the capacity of the lanes of the cable is not sufficient for the required data rate, i.e. in order to reduce the data rate. If a predefined threshold of one parameter needs to be maintained above a threshold, it may be expedient to decrease or reduce another parameter in order to accommodate for the reduced capacity of the cable when a lane is faulty. For example, if the quality of the ultrasound images cannot be maintained above a predefined threshold due to a reduced data rate capacity in the cable, it may be an option to reduce the frame rate in order to enable the maintaining of the threshold and vice versa. This can be done automatically, e.g. if an insonification scheme has been selected by the user which is not usually used for fast-moving organs such as the heart. In other applications, e.g. when the heart is being imaged, the system may reduce the size of the imaging region by "zooming in" on the center of the imaging region, where presumably the object of interest is located. Therefore, it may be possible to flexibly react to the requirements of a measurement and adapt various parameters in a way that makes sure that all the minimum requirements for the measurement are met.

In one embodiment, such adjustments to the insonification scheme are made automatically according to a pre-determined decision-tree (e.g., for each insonification scheme, the parameter that should be reduced first is pre-determined). According to another embodiment, the system is adapted to, in response to the detection of a faulty lane, allow a user to choose in which way the insonification scheme is to be changed, in particular to choose between reducing the frame rate, decreasing the spatial resolution and/or reducing the size of the imaging region. Hence, a user may change the insonification scheme according to his/her actual needs at the moment. For example, the user might decide that one parameter is more crucial than another and hence adapt the insonification scheme. For example, the user might decide that the resolution of the observed image is vital to distinguish different aspects of an observed object, while at the same time the imaging region may be reduced in size because all necessary parts are within a smaller image frame. Thus, the system remains flexible and able to react to the actual requirements that are or seem most important for a user, even in the case of a faulty lane.

According to an embodiment, the system is adapted to issue an alert through a user interface of the ultrasound system, if the overall image quality and/or the frame rate (or refresh rate) cannot be maintained above predefined thresholds. Thus, the system may continue to operate, possibly with reduced frame rate or image quality, but the user is notified that a repair or replacement of the cable may be necessary in the near future. Furthermore, the user is made aware of a possible problem with the image quality or frame rate and may for example know that important aspects, which are usually visible during a measurement, might possibly be indiscernible at the moment. Hence, it is avoided that the user is misled into drawing false conclusions (i.e. assuming a feature of an anatomical structure is missing or part of an organ is moving too slowly) due to the reduced image quality or frame rate/refresh rate. The user may then, for example, initiate a suitable service event, such as replacement, field cable replacement or repair of the cable. It is also conceivable to issue an alert to the user after detection of faulty lane and independent of any thresholds. This may make the user aware, that the cable may be damaged and that further damage or a greater data rate needed for another application may impact the performance of the cable or the system.

According to an embodiment, in response to the detection of a faulty lane, the system is adapted to modify the signals carried by the one or more non-faulty lanes by omitting the signal received by at least one transducer element, or by combining the signals received by a plurality of transducer elements. The omission may be useful if it is clear that the signal from one transducer element is less important than others for the beamforming operation. Combining of a plurality of signals may be done, for example, by adding together the signals from two or more adjacent transducer elements, possibly as a weighted sum, and/or by beamforming, i.e. delaying one element's signals before summing (with or without weighting). In particular the US probe may communicate to the data processing module or the console in general that a sum or a beamformed signal is transmitted in order to allow incorporation of the respective signal into the overall beamsum appropriately, i.e. not as if the signal came from one of the functional transducer elements.

According to an embodiment, the cable has a first number of lanes, and the cable is operatively coupled to the ultrasound probe on one end and to a system interface on the other end, and wherein the system interface is adapted to carry a second number of lanes, wherein the second number is smaller than the first number, and wherein the fault detection module is adapted to detect or receive information on which cable lanes are not connected to the system interface, and mark lanes that have no connection as faulty lanes. Thus, the system is not only able to detect and react to faulty lanes but also to lanes that are not connected due to limitations of the system. E.g., on power-up, the US probe may identify the number of available lanes and configure the communication accordingly. This advantageously allows the use of different cables with differing numbers of lanes with a common US probe. Another useful application is the use of a common US probe with different US systems and data processing units, even if the respective system interfaces do not provide the same number of connections or pins as the US probe or as the number of cable lanes. In this case an adapter may be used to connect a cable with a higher number of lanes to a data processing unit with a lower number of lanes. In other words, the US system console or data processing unit may have connectors with M lanes, while the cable and the US probe have N lanes, wherein M<N. In some embodiments, either the US system console or the data processing unit has an internal reconfiguration module that allows connection of the cable with N lanes to the US system console or data processing unit with M connections, or an external reconfiguration module (such as an adapter), which connects N lanes of the cable to M connectors, is used. In analogue systems, internal and external analogue multiplexers may be used instead. In this context the case M>N is also conceivable, wherein the reconfiguration module may be simply a pass-through for N lanes to N of the M data processing unit lanes. The case of M=N is the trivial pass-through case that does not need any additional configuration.

Yet another aspect of the invention concerns a method for operating an ultrasound probe, the ultrasound probe being configured to be operatively coupled to a cable, the cable comprising a plurality of lanes adapted to carry signals from the ultrasound probe to a data processing unit, which is adapted to process the signals, in particular to beamform the signals and to reconstruct ultrasound images of an imaging region insonified by the ultrasound probe;

the method comprising the steps of:
monitoring integrity of each of the plurality of lanes;
detecting or receiving information on the integrity of each of the plurality of lanes; and
responsive to the detection of a faulty lane, redistributing and/or reconfiguring the signals carried by the faulty lane onto one or more of the non-faulty lanes.

The monitoring of the plurality of lanes and detection of a faulty lane is preferably carried out as explained above, and preferably by the fault detection module. The redistribution and reconfiguration is also as explained herein and is preferably carried out by the controller. All the advantages and features of the US probe and the system also apply for the method and vice versa.

BRIEF DESCRIPTION OF THE DRAWINGS

The invention shall now be illustrated by means of embodiments with reference to the attached drawings, in which.

DESCRIPTION OF EMBODIMENTS

Throughout the figures, the same or corresponding features/elements of the various embodiments are designated with the same reference numbers.

Figure 1:
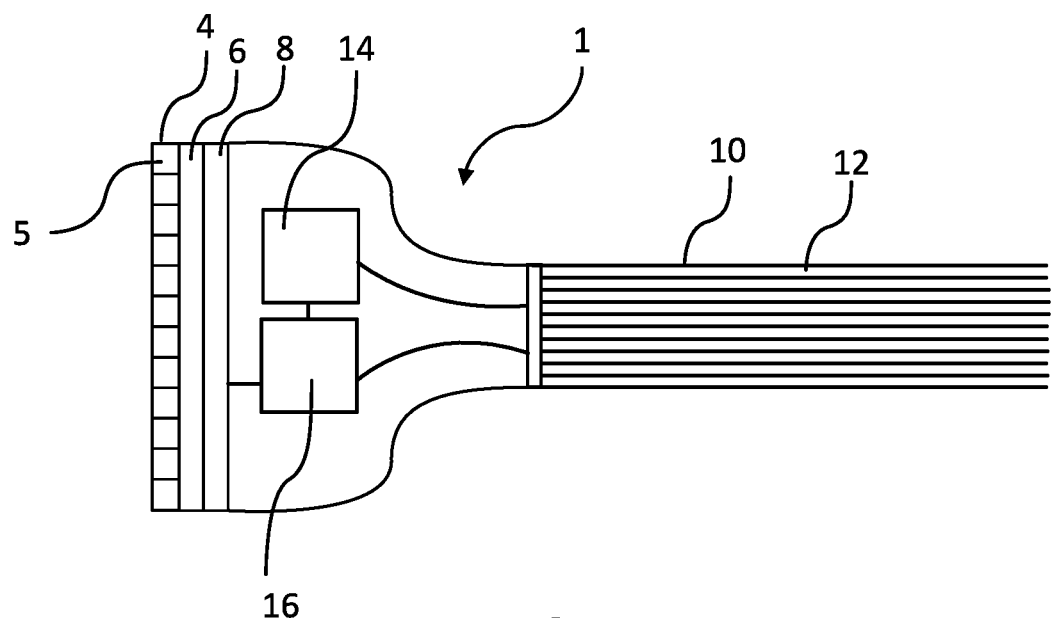
FIG. 1 shows a schematic illustration of an ultrasound probe according to an embodiment of the invention.
Figure 2:
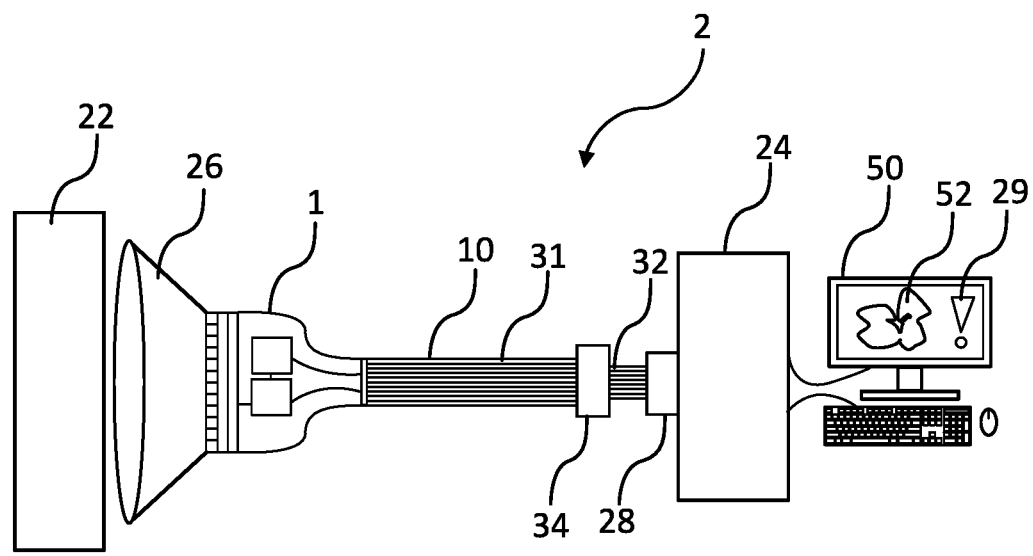
FIG. 2 shows a schematic illustration of a system according to an embodiment of the invention.

FIG. 1 shows a schematic illustration of an ultrasound (US) probe 1 according to an embodiment of the invention and a cable 10 with several lanes 12. The main task of the cable 10 is to carry signals 42 between the US probe 1 and a data processing unit 24, as shown in FIG. 2. The US probe comprises a transducer head 4 with transducer elements 5, which are adapted to insonify an imaging region 22 according to an insonification scheme 26 and to receive echo signals. Placed next to the transducer elements 5 is an analogue-to-digital converter (ADC) 6 that is adapted to convert incoming analogue echo signals into digital signals. Next to the ADC 6 is a buffer that is adapted to (optionally) buffer the digitized signals. Preferably, the ADC 6 consists of an array of ADCs and the buffer 8 may constitute an array of buffers, wherein one ADC and/or buffer 8 is present for each one or a sub-group of transducer elements 5. In case of a high-speed serial data link, the data of multiple ADCs may be collected and transferred across one data lane. The transducer elements 5, the ADC 6 and the buffer 8 are in connection with a controller 16. The controller 16 is configured to be connected to the data processing unit 24 via the cable 10 or via a lane 12 of the cable 10. Furthermore, the controller is connected to a fault detection module 14. In this embodiment, the fault detection module is disposed within the US probe 1; in other embodiments it may be part of the US console. The fault detection module 14 is also in contact with the lanes 12 of the cable 10 and adapted to detect information on the integrity of each of the lanes. Thus, preferably the fault detection module 14 may detect a faulty lane 13 by itself, for example during a self-check of the US probe 1, or alternatively it may be adapted to receive information about a faulty lane 13 via the cable 10 from the data processing unit 24 to which it is connected. When the fault detection module 14 has information about a faulty lane 13, it transmits this information to the controller 16, which is configured to then redistribute and/or reconfigure the signals 42 originally intended to be carried by the faulty lane 13 onto one or more of the non-faulty lanes 12.

FIG. 2 shows a schematic illustration of a system 2 according to an embodiment of the invention. The system 2 comprises a US probe 1 as shown in FIG. 1, a data processing unit 24 and a cable 10. The cable 10 is coupled to the US probe 1 and the data processing unit 24 and adapted to carry signals between the US probe 1 and the data processing unit 24. The US probe 1 is configured to insonify an imaging region 22 according to an insonification scheme (schematically shown at 26), to receive and process echo signals and transmit signals based on the echo signals to the data processing unit 24. Processing of echo signals in the US probe comprises converting the echo signals to digital signals 42 with the ADC 6 and possibly buffering the signals 42 with the buffer 8. The system is configured to transfer the signals from the US probe to the data processing unit 24 via the cable 10. In this embodiment the cable 10 has a first number of lanes 31 and the data processing unit 24 has a system interface 28 that is adapted to be connected to a cable with a second number of lanes 32, wherein the first number of lanes 31 is greater than the second number of lanes 32. Hence, in this example, the cable 10 is connected to the data processing unit 24 via an adapter 34. However, in other embodiments an adapter 34 will not be necessary. The fault detection module 14 of the US probe 1 is adapted to automatically notice the difference in the number of lanes 12 and mark lanes 12 of the cable 10 that have no connection as faulty lanes 13. Hence the US probe 1 is able to adapt to the lower number of lane connections on the data processing unit's side. The data processing unit 24 is adapted to process the signals 42 received from the US probe 1 and in particular to beamform the signals 42 and reconstruct US images 52 of the imaging region 22. The system is furthermore configured to display the US images 52 on a user interface 50. In the case of a faulty lane 13, the system 2 is adapted to change the insonification scheme 26, for example by reducing the frame rate, reducing the sampling frequency, decreasing the spatial resolution or reducing the size of the imaging region 22. It is also conceivable to increase the number of insonification events in order to collect the data of the faulty or missing lane or lanes 13 during a next insonification cycle. This change of the insonification scheme 26 may also be influenced, changed or initiated by a user 36 via the user interface 50 comprising a computer screen, a keyboard and a mouse. The system 2 also comprises an alert function 29, wherein a user 36 is notified of a faulty lane 13. Furthermore, the user 36 will receive an alert 29 if the overall image quality and/or frame rate cannot be maintained above predefined thresholds. This may for example be important if the quality of the measured US images 52 is no more sufficient for the intended use due to one or several faulty lanes 13.

Figure 3:
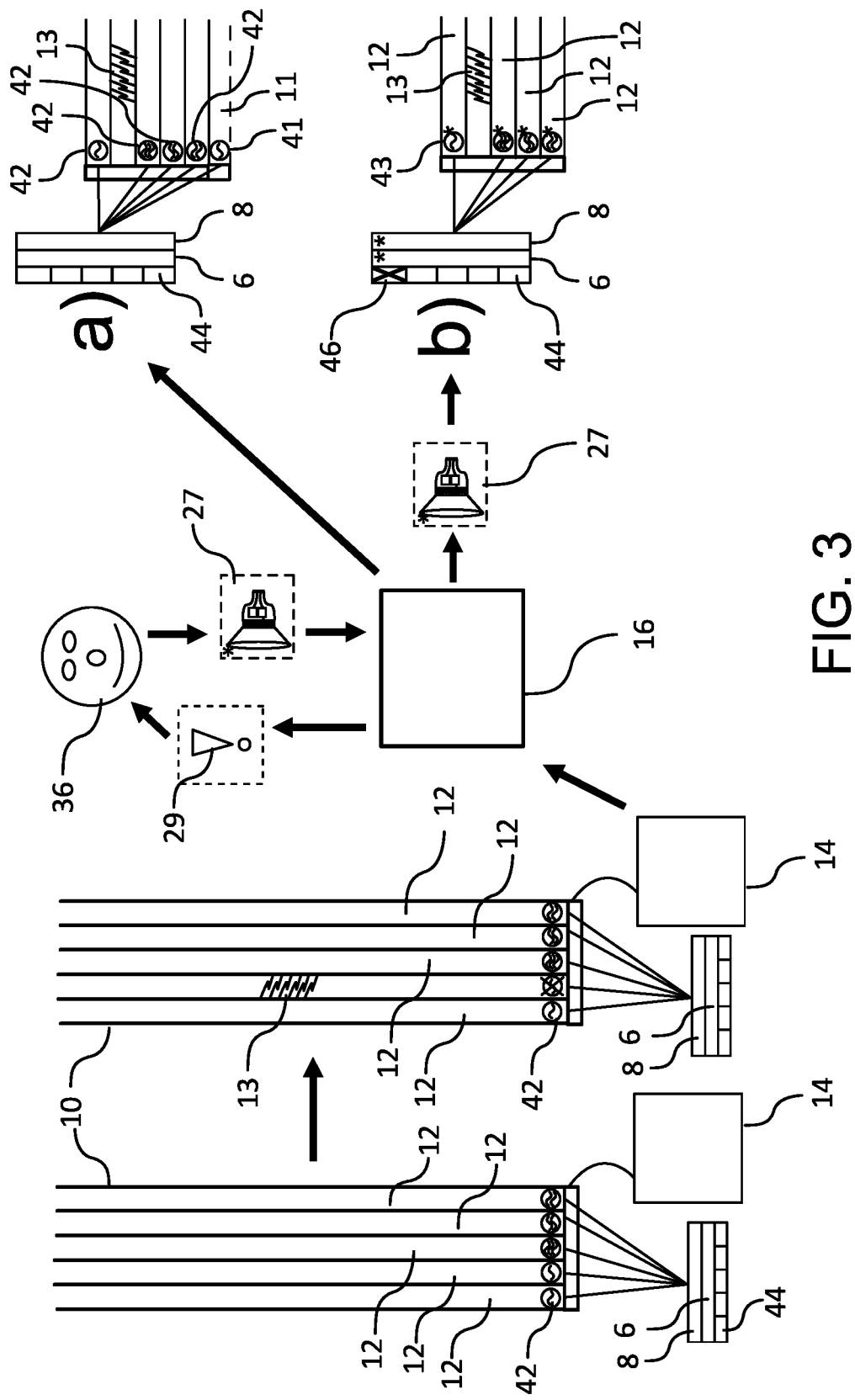
FIG. 3 schematically shows the working principle of an embodiment of the invention.

FIG. 3 schematically shows the working principle of an embodiment of the invention in the case of the occurrence of a faulty lane 13. On the left side, five lanes 12 of the cable 10 are used in operation and fully able to carry the signals 42 received by the transducer elements 5 of the transducer head 4. The number of five lanes is only exemplary in this case to illustrate the general principle. The actual number of lanes may vary and be in particular higher than five. The signals are digitized by the ADC 6 and may be buffered by the buffer 8. Hence, the fault detection module 14 will not notice any irregularity or fault at this stage. In the next scenario shown right next to the intact cable 10, one of the five lanes 12 is faulty 13, for example due to excessive strain on the cable 10. While the four non-faulty lanes 12 are still capable of carrying their signals 42, the faulty lane 13 cannot carry a signal anymore. The faulty lane 13 is detected by the fault detection module 14 and information of this faulty lane is transmitted to the controller 16. On the right side of FIG. 3 there are shown several options that may be initiated by the controller 16. While in this embodiment the controller 16 is configured to be able to carry out all these actions, it does not necessarily have to apply all of the actions at the same time but only initiate the ones that are most useful given the circumstances. The actual measures to be taken may for example be programmed on the controller 16, e.g. in the form of an algorithms and/or logic functions. It is also conceivable that another controller 16 according to the invention is only configured to carry out some of the actions shown in FIG. 3. The controller 16 may send an alert 29 to a user 36, in order to notify the user about the faulty lane 13. Apart from this, there are generally two main options available for the controller 16. The first one, denoted a), being available if the cable 10 has a redundant lane 11 that is fully operational but was not needed previously since the data rate was low enough so that five lanes were sufficient. In this case the controller 16 may re-route the signal 41, that was originally intended to be carried by the faulty lane 13 to the redundant lane 11. This may allow the operation of the US probe 1 and the transmission of the signals 41, 42 to the data processing unit 24 without any impact on image quality or frame rate. However, if no redundant lane 11 is available, the controller may reconfigure or modify the existing signals 42, according to option b), in order to include information originally carried by the faulty lane 13 within the reconfigured and/or redistributed signals 43. If the capacities of the remaining four lanes 12 is not sufficient to carry all the information that was originally intended to be carried by five lanes 12, the data rate needs to be reduced. This may for example be achieved by changing the insonification scheme, e.g. by reducing the frame rate, reducing the sampling frequency, decreasing the spatial resolution or reducing the size of the imaging region. It may also be an option to allow a user to choose in which way the insonification scheme 27 is to be changed. For example, the user may choose which parameters are the least important at this moment and may be reduced the most, e.g. the user might decide that the frame rate and resolution are vital to the measurement while the size of the imaging region may be decreased. Preferably this reconfiguration is done while at the same time maintaining the image quality and frame rate above predefined or user input thresholds. The system 2 may adapt some parameters, e.g. of the insonification scheme 26, in order to allow other parameters to remain above their respective threshold. If the overall image quality and/or frame rate cannot be maintained above those predefined thresholds the system 2 is configured to send an alert 29 to the user 36 via a user interface 50. Furthermore, the controller 16 might initiate the omission of one echo signal received by a transducer element 5 at a time, which carries less essential information. Further measures may include, prior to redistributing and reconfiguring the signals 42, to decrease the bit depth or sampling frequency of the ADC 6 for at least some of the signals 44 or suppressing the least-significant bit of each digitized signal sample. Additionally, it may also be an option to buffer at least a part of the digital signals from the ADC 6 in the buffer 8, in particular the signals originally carried by the faulty lane 13, while the transducer elements 5 corresponding to the signals 44 are receiving echo signals, and stream out the buffered signals during dead time of the transducer elements 5, in particular in the dead time between the end of one receive event and the beginning of the following transmit event.

Figure 4:
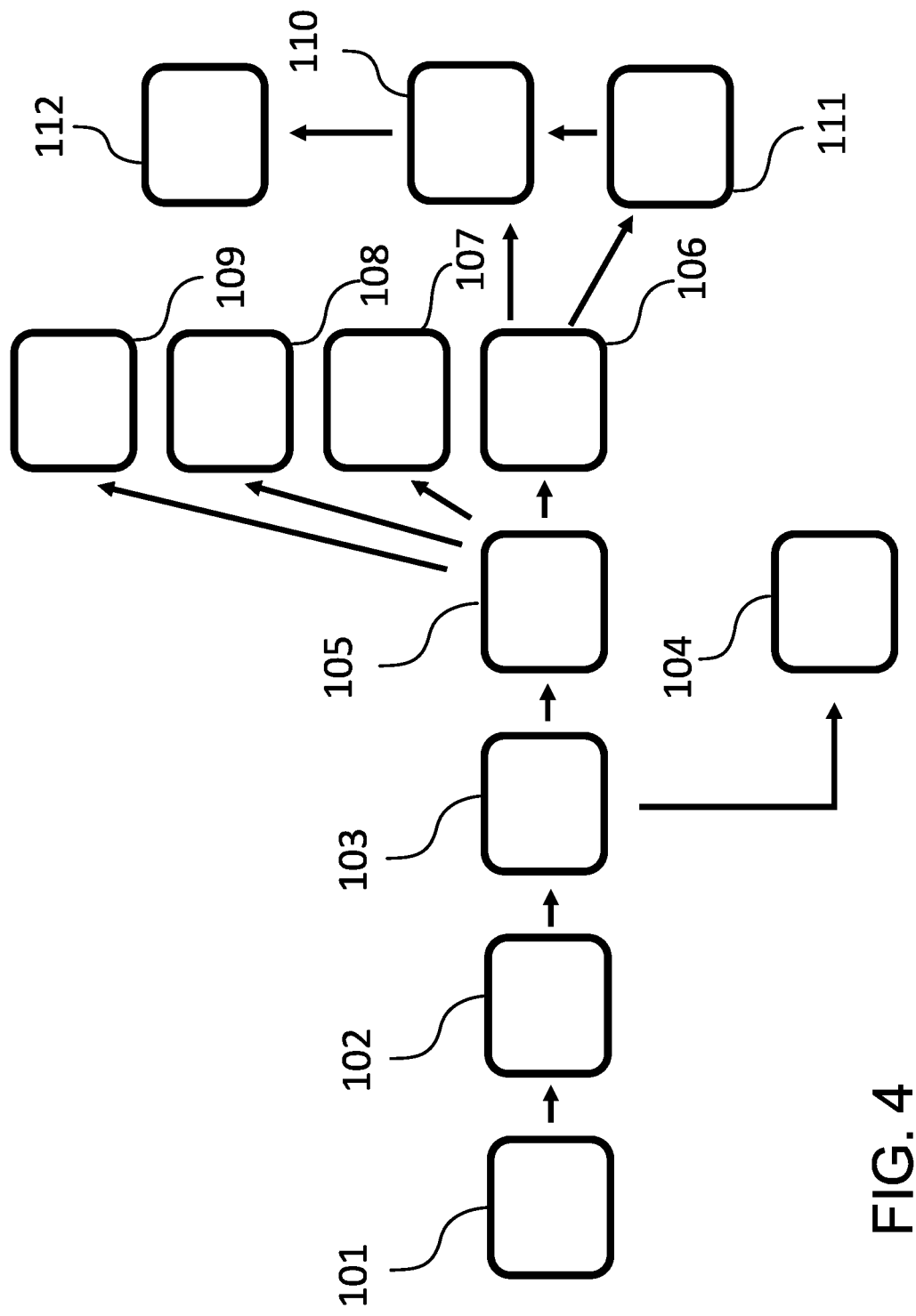
FIG. 4 shows a flow diagram representing a method according to an embodiment of the invention.

FIG. 4 shows a flow diagram representing a method according to an embodiment of the invention. The method comprises a first step of monitoring the integrity of each of the plurality of lanes 101 by the fault detection module 14. The next step comprises detecting or receiving information on the integrity of each of the plurality of lanes 102. If at least one faulty lane 13 is detected, step 103, the signals carried by the faulty lane 13 are either re-routed to a redundant lane 11, step 104, or the signals carried by the one or more non-faulty lanes are modified so as to include information related to the signal originally carried by the faulty lane 13, step 105. Step 105 may be further adapted to include additional options. For example, a further step 106 may comprise maintaining the quality of the ultrasound images 52 and/or the frame rate of the ultrasound images 52 above predefined thresholds. In order to achieve step 106, step 110 may be applied, i.e. changing the insonification scheme 26 so that the predefined thresholds are met. Changing the insonification scheme 26 may comprise one or more of reducing the frame rate, reducing the sampling frequency, decreasing the spatial resolution or reducing the size of the imaging region. Optionally, in step 111, a user may be given the option to choose in which way the insonification scheme 26 is to be changed. If the predefined threshold cannot be maintained, step 112 may be applied, which comprises issuing an alert 29 through a user interface 50. Further options for step 105 are decreasing the ADC bit depth or sampling frequency, step 107, suppressing the least-significant bit of each digitized signal sample, step 108, and/or buffering the signals 41 originally carried by the faulty lane 13 and streaming out the buffered digital signals during dead time of the transducer elements, step 109.

Figure 5:
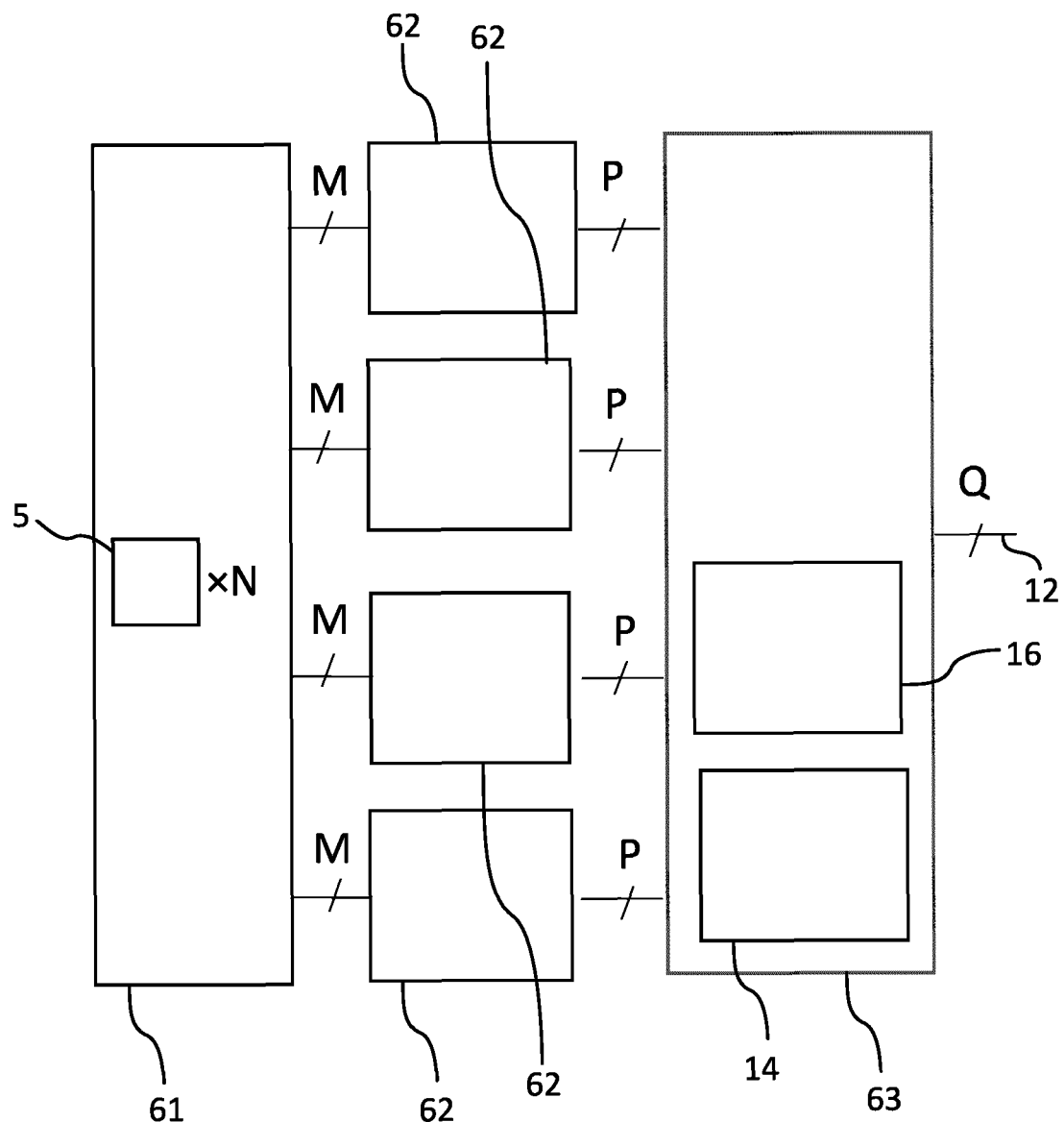
FIG. 5 shows a schematic representation of an implementation of the US-probe according to an embodiment of the invention.

FIG. 5 shows a schematic representation of an implementation of the US probe according to an embodiment of the invention. In this embodiment, there is a transducer array 61 located in the transducer head 4 with N transducer elements 5. Analogue signals from these N transducer elements 5 are distributed to four ASICs each having an ADC array 62 with M ADCs. In this case N=4×M, however, there may be more than 4 ADC arrays 62. Hence, an equal number of analogue signals, namely M analogue signals, is converted on each ASIC by its respective ADC array 62. For example, there may be M=32 ADCs on each ASIC providing AD conversion for N=4×32=128 analogue signals from N=128 transducer elements. Each ASIC has P serial output lanes to transfer data, wherein P is lower than M and typically not very high (e.g. 2-8), so that every lane may carry the data of M/P transducer elements (channels). For example, each ASIC may have P=4 serial output lanes, each carrying the data of M/P=8 channels. Using several, in this example four, ASICs instead of one large ASIC with more ADCs has the advantage of not yielding packaging issues, avoiding problems with power dissipation and providing the possibility of modularity. The number of ASICs with M ADCs may be adapted to the actual number of transducer elements 5 of the US probe 1. Hence, a US probe 1 comprising a larger number of transducer elements 5 may have more ASICs with M ADCs each. For example, a high-end US probe 1 may have far more than 32 transducer elements (analogue channels) and thus require multiple ASICs. In order to combine the data of the various ASICs, taking into account the point-to-point character of high-speed interfaces, there is provided a data collector unit 63 in this embodiment. The data collector unit 63 is configured to combine the data from the different ASICs and distribute it over the available lanes 12. The number of available lanes 12 is Q, wherein Q is typically different and preferably smaller than P times the number of ADC arrays 62. The data collector unit 63 may also be replaced by a switch matrix. In this embodiment, the data collector unit 63 comprises both the controller 16 and the fault detection module 14. In such an embodiment, it is expedient to have a robust connection between the ASICs comprising the ADC arrays 62 and the data collection unit 63 that is not sensitive to defects. The fault detection module 14 may also be located elsewhere, e.g. in the console. It may also be conceivable that the ASICs 62 comprise a controller 16 and/or a fault detection module 14 each. However, the options for rerouting signals may be limited in such a case because the number of lanes from the ASICs may be limited. If the ADC arrays 62 transfer high-speed serial data, this may involve data encoding to allow for word and frame synchronization since the receiver (i.e. the data collector unit 63) needs to know where a word or frame starts and ends. Advantageously, if data only needs to be transferred across a short distance, this allows to reduce the power dissipation involved in the data transmission. For example, lower signal swings may be used. Also, the data protocol may be simple. Potentially the data speed from the ADC may vary from the data speed across the cable lanes 12. ADC lane speed may be real time, i.e. there is no memory storage in the ADC arrays 62. The data collector unit 63 may perform the redistribution and/or reconfiguration of the signals carried from the US probe 1 to the data processing unit 24, in particular the data from the ADC arrays 62. Optionally, the data collector unit may also comprise a memory function that may be beneficial for a flexible rerouting of the data. Therefore, the data stream from the data collection unit 63 through the lanes 12 may run at a faster or slower pace depending on the connected system. Likely, the data protocol may be more complex to indicate the organization of the transmitted data. The data collector unit 63 may for example be a Field Programmable Gate Array (FPGA) with a large amount of GTX transceivers or MIPI D-PHY lanes (supporting CSI camera interfaces) or may be a dedicated additional ASIC.

The above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

LIST OF REFERENCE SIGNS 1 ultrasound probe
2 ultrasound system
4 transducer head
5 transducer element
6 analogue-to-digital converter
8 buffer
10 cable
11 redundant lane
12 lane
13 faulty lane
14 fault detection module
16 controller
22 imaging region
24 data processing unit
26 insonification scheme
27 changed insonification scheme
28 system interface
29 alert
31 first number of lanes
32 second number of lanes
34 adapter
36 user
41 signal originally carried by faulty lane
42 signals
43 reconfigured/redistributed signals
44 echo signals received from each transducer element
46 omitted signals
50 user interface
52 ultrasound image
61 transducer array
62 analogue-to-digital converter array
63 data collector unit
101-112 method steps

The invention claimed is:

1. An ultrasound probe configured to be operatively coupled to a cable, the cable comprising a plurality of lanes adapted to carry signals between the ultrasound probe and a data processing unit, which is configured to beamform the signals and to reconstruct ultrasound images of an imaging region, the ultrasonic probe comprising:
a transducer head comprising a plurality of transducer elements, wherein the plurality of transducer elements are configured to insonify the imaging region according to an insonification scheme and to receive ultrasound signals; and
a controller configured to receive integrity information on integrity of each lane of the plurality of lanes from a fault detection module, wherein the fault detection module is configured to detect integrity or faultiness of each lane of the plurality of lanes, and wherein the controller is further configured to, responsive to the integrity information indicating a faulty lane from the fault detection module, modify the signals carried by the one or more non-faulty lanes that are carrying the signals from one or more of the plurality of transducer elements, respectively, to include information from the signals originally carried by the faulty lane, wherein modifying the signals includes increasing a data rate of the one or more non-faulty lanes and/or reducing information from the faulty lane.

2. The ultrasound probe according to claim 1, wherein the controller is further configured to redistribute the signals carried by the faulty lane by also re-routing the signals carried by the faulty lane to a redundant lane of the plurality of lanes.

3. The ultrasound probe according to claim 1, wherein the controller is further configured to modify the signals carried by the one or more non-faulty lanes while maintaining quality of the ultrasound images and/or a refresh rate of the ultrasound images above predefined thresholds, respectively.

4. The ultrasound probe according to claim 1, further comprising:
an analogue-to-digital converter configured to convert the ultrasound signals received by the plurality of transducer elements into digital signals,
wherein, responsive to the integrity information indicating the faulty lane from the fault detection module, the analogue-to-digital converter is configured to decrease bit depth or sampling frequency, and the controller is configured to modify the signals carried by the non-faulty lanes so as to include digital signals originally carried by the faulty lane.

5. The ultrasound probe according to claim 1, further comprising:
an analogue-to-digital converter configured to convert the ultrasound signals received by the plurality of transducer elements into digital signals,
wherein, responsive to the integrity information indicating the faulty lane from the fault detection module, the controller is configured to modify the signals carried by the non-faulty lanes so as to include digital signals originally carried by the faulty lane, wherein reducing the information from the faulty lane includes suppression of a least-significant bit of cach digitized signal sample.

6. The ultrasound probe according to claim 1, further comprising:
an analogue-to-digital converter configured to convert the ultrasound signals received by the transducer elements into digital signals, and an in-probe memory configured to buffer the digital signals,
wherein the signals carried by the non-faulty lanes are modified so as to include digital signals originally carried by the faulty lane,
wherein the in-probe memory is configured to buffer at least a part of the digital signals received from the analogue-to-digital converter during a receive event of the transducer elements, and wherein the controller is further configured to stream out the buffered digital signals also during dead time of the transducer elements, wherein the dead time is between an end of one receive event and a beginning of a following transmit event.

7. The ultrasound probe according to claim 6,
wherein the in-probe memory is configured to buffer the digital signals originally carried by the faulty lane while the plurality of transducer elements are receiving the ultrasound signals, and
wherein the controller is further configured to stream out the buffered digital signals originally carried by the faulty lane during the dead time of the transducer elements, wherein the dead time is between the end of one receive event and the a beginning of the following transmit event.

8. An ultrasound system comprising:
the ultrasound probe of claim 1;
the data processing unit, which is configured to beamform the signals and to reconstruct the ultrasound images of the imaging region;
the fault detection module configured to detect the integrity information on the integrity or the faultiness of each lane of the plurality of lanes; and
the cable operatively coupled to the ultrasound probe, the cable comprising the plurality of lanes configured to carry the signals between the ultrasound probe and the data processing unit.

9. The ultrasound system of claim 8, wherein, when quality of the ultrasound images and/or a refresh rate cannot be maintained above predefined thresholds, respectively, the system is configured to change the insonification scheme so that the predefined thresholds are met.

10. The ultrasound system of claim 8, wherein the system is configured to change the insonification scheme by one or more of reducing a frame rate, reducing a sampling frequency, decreasing a spatial resolution or reducing a size of the imaging region.

11. The ultrasound system of claim 8, wherein the system is configured to, in response to the detection of the faulty lane, allow a user to choose among reducing a frame rate, decreasing a spatial resolution and/or reducing a size of the imaging region.

12. The ultrasound system of claim 8, wherein, in response to the detection of the faulty lane, the system is configured to modify the signals carried by the one or more non-faulty lanes by omitting at least one signal received by at least one transducer element of the plurality of transducer elements, or by combining the signals received by the plurality of transducer elements, so as to reduce an overall amount of data to be carried by the non-faulty lanes.

13. The ultrasound system according to claim 8, wherein the cable has a first number of lanes, and the cable is operatively coupled to the ultrasound probe on one end and to a system interface on the other end, and wherein the system interface is configured to carry a second number of lanes, wherein the second number is smaller than the first number, and
wherein the fault detection module is configured to detect or receive information on which cable lanes are not connected to the system interface, and mark lanes that have no connection as faulty lanes.

14. The ultrasound system according to claim 8, wherein, when overall image quality and/or a frame rate cannot be maintained above predefined thresholds, respectively, the system is configured to issue an alert through a user interface of the ultrasound system.

15. A method for operating an ultrasound probe, the ultrasound probe being configured to be operatively coupled to a cable, the cable comprising a plurality of lanes configured to carry signals from the ultrasound probe to a data processing unit configured to beamform the signals and to reconstruct ultrasound images of an imaging region insonified by the ultrasound probe the method comprising:
monitoring integrity of each lane of the plurality of lanes;
detecting or receiving integrity information on the integrity of each lane of the plurality of lanes; and
responsive to detection of a faulty lane of the plurality of lanes, redistributing and reconfiguring the signals carried by the faulty lane onto one or more non-faulty lanes of the plurality of lanes of the plurality of lanes that are carrying the signals from the ultrasound probe, and modifying the signals carried by the one or more non-faulty lanes so as to include information from the signals originally carried by the faulty lane, wherein modifying the signals includes increasing a data rate of the one or more non-faulty lanes and/or reducing information from the faulty lane.

16. The method of claim 15, further comprising:
when quality of the ultrasound images and/or a refresh rate cannot be maintained above predefined thresholds, respectively, by redistributing and reconfiguring the signals after the detection of the faulty lane, changing an insonification scheme of the ultrasound probe so that the predefined thresholds are met.

17. The method of claim 15, further comprising:
changing an insonification scheme of the ultrasound probe by reducing a frame rate, reducing a sampling frequency, decreasing a spatial resolution, and/or reducing a size of the imaging region.

18. The method of claim 15, further comprising:
in response to the detection of the faulty lane, enabling selection among reducing a frame rate, decreasing a spatial resolution and/or reducing a size of the imaging region.

19. The method of claim 15, wherein modifying the signals carried by the one or more non-faulty lanes further comprises omitting at least one signal received by at least one transducer element in a plurality of transducer elements of the ultrasound probe, or combining signals received by the plurality of transducer elements, so as to reduce an overall amount of data to be carried by the one or more non-faulty lanes.

20. An ultrasound system comprising:
an ultrasound probe comprising a transducer head including a plurality of transducer elements and an analog-to-digital converter (ADC), wherein the plurality of transducer elements are configured to insonify an imaging region and to receive echo signals in response, and the ADC is configured to convert the echo signals into digital signals;
a cable coupled to ultrasound probe, wherein the cable comprises a plurality of lanes configured to carry the digital signals from the ultrasound probe;
a data processing unit configured to receive the digital signals via the cable and to reconstruct ultrasound images of the imaging region from the digital signals;
a fault detection module configured to detect integrity information of each lane of the plurality of lanes of the cable; and
a controller configured to:
receive the integrity information from the fault detection module, responsive to the integrity information indicating a faulty lane of the plurality of lanes of the cable, redistribute and reconfigure digital the signals carried by the faulty lane onto one or more non-faulty lanes of the plurality of lanes that are carrying digital the signals from the ultrasound probe, and modify the digital signals carried by the one or more non-faulty lanes so as to include information from the digital signals originally carried by the faulty lane, wherein modifying the digital signals includes increasing a data rate of the one or more non-faulty lanes and/or reducing information from the faulty lane.

* * * * *